(12) United States Patent
Saegusa et al.

(10) Patent No.: US 7,162,913 B2
(45) Date of Patent: Jan. 16, 2007

(54) METHOD OF EVALUATING RESTITUTION CHARACTERISTIC OF GOLF CLUB, SYSTEM FOR EVALUATING RESTITUTION CHARACTERISTIC, AND GOLF CLUB

(75) Inventors: Hiroshi Saegusa, Kanagawa (JP); Kazunori Ono, Kanagawa (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 442 days.

(21) Appl. No.: 10/187,891

(22) Filed: Jul. 3, 2002

(65) Prior Publication Data

US 2004/0005938 A1    Jan. 8, 2004

(51) Int. Cl.
*G01L 5/00* (2006.01)
*A63B 53/00* (2006.01)

(52) U.S. Cl. .................. 73/11.01; 73/65.03
(58) Field of Classification Search .......... 73/570, 73/65.03, 11.01–12.14
See application file for complete search history.

(56) References Cited

U.S. PATENT DOCUMENTS

| | | | |
|---|---|---|---|
| 4,543,827 A * | 10/1985 | Tominaga et al. | 73/602 |
| 4,870,868 A * | 10/1989 | Gastgeb et al. | 73/649 |
| 4,928,965 A | 5/1990 | Yamaguchi et al. | 273/78 |
| 5,703,294 A * | 12/1997 | McConnell et al. | 73/579 |
| 5,796,005 A * | 8/1998 | Frolow | 73/651 |
| 6,142,886 A * | 11/2000 | Sullivan et al. | 473/371 |
| 6,186,002 B1 * | 2/2001 | Lieberman et al. | 73/432.1 |
| 6,289,735 B1 * | 9/2001 | Dister et al. | 73/579 |
| 6,527,648 B1 * | 3/2003 | Erickson et al. | 73/570 |
| 6,595,057 B1 * | 7/2003 | Bissonnette et al. | 73/579 |
| 2002/0183136 A1 * | 12/2002 | Helmstetter et al. | 473/345 |
| 2002/0189356 A1 * | 12/2002 | Bissonnette et al. | 73/570 |

FOREIGN PATENT DOCUMENTS

| | | |
|---|---|---|
| GB | 2 377 498 A | 1/2003 |
| JP | 61-22875 | 1/1986 |
| JP | 8-224328 | 9/1996 |
| JP | 3043639 | 9/1997 |
| WO | WO 02/081036 A1 | 10/2002 |

* cited by examiner

*Primary Examiner*—Max Noori
(74) *Attorney, Agent, or Firm*—Finnegan, Henderson, Farabow, Garrett & Dunner, L.L.P.

(57) ABSTRACT

A method of evaluating restitution characteristics of a golf club head, a system for evaluating the restitution characteristics and a golf club, are provided in which a coefficient of restitution of a golf club head is inferred and obtained without disassembling the golf club by removing the golf club head away from a shaft and the coefficient of restitution may extremely easily be obtained for a short period of time. At first, an external force to a striking face of the golf club head is imparted to perform impact vibration. A response signal of the striking face under the impact vibration is acquired to obtain a resonant frequency of the striking face. A coefficient of restitution is calculated from the resonant frequency when the golf ball is struck by the striking face, whereby restitution characteristics of the golf club head are inferred and evaluated.

14 Claims, 6 Drawing Sheets

METHOD OF EVALUATING RESTITUTION CHARACTERISTIC OF GOLF CLUB, SYSTEM FOR EVALUATING RESTITUTION CHARACTERISTIC, AND GOLF CLUB

BACKGROUND OF THE INVENTION

1. Field of the Invention

The present invention relates to a method of evaluating restitution characteristics of a golf club head which evaluates restitution characteristics of a striking face of the golf club head when a golf ball is struck by the golf club head such as a hollow golf club head made of metal or the like, and relates to a system for evaluating the restitution characteristic, and a golf club.

2. Description of the Related Art

Recently, through improvement and development of structures and materials of golf club heads, golf club manufacturers have proposed a variety of golf clubs having a golf club head with high restitution characteristics so that even a golfer who with weak power may hit a golf ball far.

Figure 8:
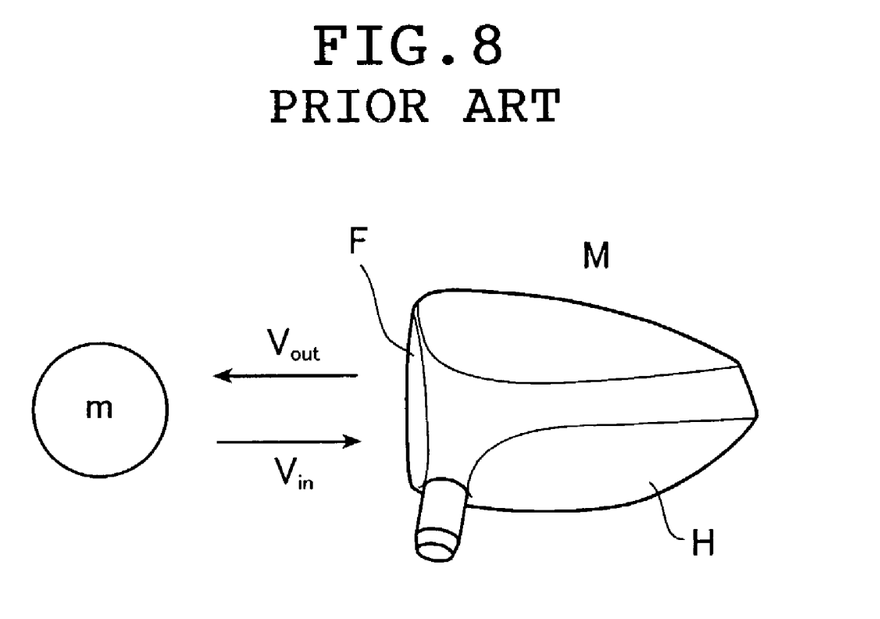
FIG. 8 is a view illustrating a conventional measuring method of measuring a coefficient of restitution.

On the other hand, the United States Golf Association (USGA) promulgates a rule for regulating the golf club that may hit the golf ball too far due to the excessively high restitution characteristics in a professional golf tournament of professional golfers, and stipulates that the golf club with a coefficient of restitution e, obtained by the following method below, of 0.830 or less should be used in the professional golf tournament. According to this, the coefficient of restitution e between the golf ball and the golf club head is given as follows. Under the condition that the golf club head H is laid on a base table, the golf ball is caused to impact perpendicularly to a face F of the golf club head H as shown in FIG. 8, and the coefficient of restitution e is obtained from the formula (indicated below) among an incoming velocity $V_{in}$ and an outgoing velocity $V_{out}$ of the golf ball, a mass M of the golf club head and a mass m of the golf ball at this time.

$$V_{out}/V_{in}=(e \cdot M-m)/(M+m)$$

However, when the coefficient of restitution e is calculated according to the above-described method, it is necessary to set the face F of the golf club head H perpendicular to an incoming direction of the golf ball and, in addition, to accurately align the golf club head H for the golf ball to strike the face F at a predetermined striking position. Also, since it is necessary to measure only with the golf club head by removing the golf club head away from the shaft, it is also necessary to perform troublesome work for disassembling the golf club and reassembling the golf club after measurement. Thus, it is almost impossible to examine the golf clubs, one by one, of the professional golfers who participate the tournament within limited time before a start of the tournament for calculating the coefficient of restitution e according to the above-described method.

Also, if the disassembled golf club is reassembled, a favorable impression which the golf club has given to the professional golfer for a long time is often changed.

SUMMARY OF THE INVENTION

Accordingly, in order to solve the above-described problems, an object of the present invention is to provide a method of evaluating restitution characteristics of a golf club head, whereby a coefficient of restitution of a golf club head without disassembling the golf club by removing a golf club head away from a shaft is inferred and obtained and the coefficient of restitution may extremely easily be obtained for a short period of time, and to provide a system for evaluating the restitution characteristics and a golf club.

In order to attain the above object, according to the present invention, there is provided a method of evaluating restitution characteristics of a golf club head, comprising: imparting an external impact force to a striking face of the golf club head at which a golf ball is hit to cause the striking face vibrating; acquiring a response signal of the striking face which vibrates by the imparted impact force thereto to obtain a resonant frequency of the striking face from the acquired response signal; and calculating a coefficient of restitution of the golf club head from the resonant frequency, the restitution being performed when a golf ball is struck by the striking face.

Here, it is preferable that the resonant frequency is a first resonant frequency of the striking face.

Further, it is preferable that the resonant frequency is a frequency from 3000 Hz to 7000 Hz.

The response signal is, for example, an acceleration signal of vibration of the striking face. In that case, it is preferable that the impact force is imparted at multiple points on the striking face, a transfer function of the acceleration signal to a signal of the impact force is obtained at each of the points, and a peak frequency at which a peak generates at the same phase in any of the obtained transfer functions at the points is obtained as the first resonant frequency.

Further, in the method it is preferable that the impact force is imparted at multiple points on the striking face, and a vibration mode at the resonant frequency is obtained by using an amplitude of a transfer function of the acceleration signal to a signal of the impact force, to evaluate a distribution of the coefficient of restitution of the striking face.

It is also preferable that the response signal is a sound pressure signal of the striking face.

According to the present invention, there is provided a system for evaluating restitution characteristics of a golf club head, comprising: an input device which acquires a response signal of a striking face of the golf club head, the striking face vibrating by an imparted impact force thereto; an analysis unit which obtains a resonant frequency of the striking face from the acquired response signal; and a calculating unit which calculates a coefficient of restitution of the golf club head, the restitution being performed when a golf ball is struck by the striking face.

The response signal is, for example, an acceleration signal of vibration of the striking face or a sound pressure signal of the striking face.

The input device, the analysis unit and the calculating unit were preferably integrated into a mobile computer.

Further, according to the present invention, there is provided a golf club, in which a restitution characteristics of a golf club head has been evaluated by using a method, comprising: imparting an external impact force to a striking face of the golf club head at which a golf ball is hit to cause the striking face vibrating; acquiring a response signal of the striking face which vibrates by the imparted impact force thereto to obtain a resonant frequency of the striking face from the acquired response signal; and calculating a coefficient of restitution of the golf club head from the resonant frequency, the restitution being performed when a golf ball is struck by the striking face.

For example, the coefficient of restitution or the evaluated restitution characteristics of a golf club head according to the present invention is disclosed in a tag or sticker attached to the golf club or a brochure.

DESCRIPTION OF THE PREFERRED EMBODIMENTS

A method of evaluating restitution characteristics of a golf club head and a system for evaluating the restitution characteristics according to the present invention will now be described in detail with reference to a preferred embodiment shown in the accompanying drawings.

Figure 1:
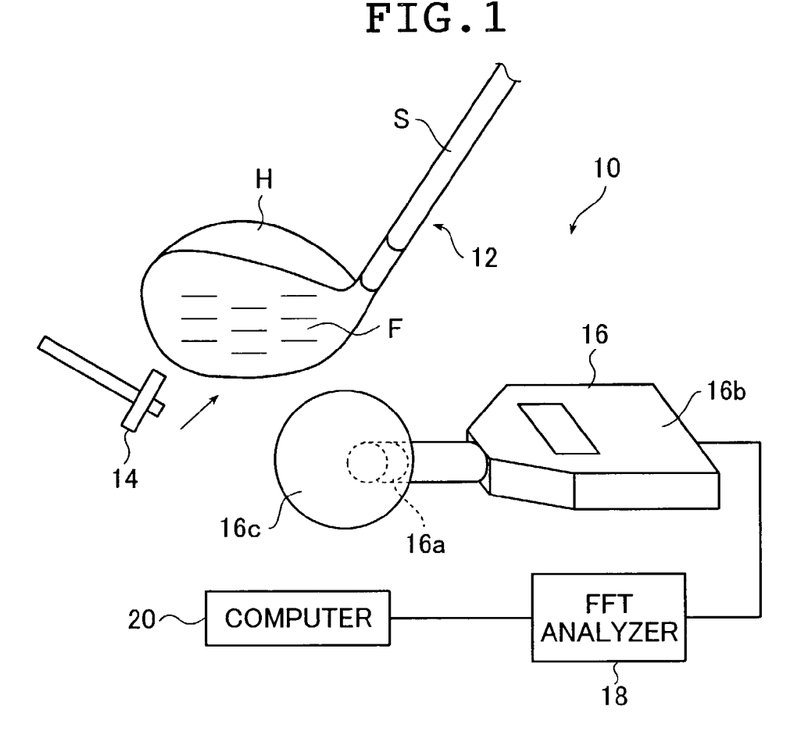
FIG. 1 is a view showing an example of an evaluation system for carrying out a method of evaluating restitution characteristics of a golf club head according to the present invention.

FIG. 1 shows an evaluation system 10 for carrying out a method of evaluating restitution characteristics of a golf club according to the present invention. The golf club to be evaluated by the evaluation system 10 is a golf club such as a driver which has a hollow golf club head made of metal or the like.

The evaluation system 10 is characterized in that restitution characteristics of a face (striking face) F may be evaluated under the condition that the golf club is integrated without removing a golf club head H away from a golf club shaft S.

The evaluation system 10 is composed of an input force jig 14 for imparting impact force, a noise measuring unit 16, an FFT (Fast Fourier Transformation) analyzer 18 and a computer 20.

The input force jig 14 is a jig for imparting the impact force to the face F of the golf club head H and a tip end of the jig is made of a metal material having such a hardness that the face F is not damaged. Also, the impact force by the input force jig 14 gives a light impact on the face F so that the face F is not damaged.

The noise measuring unit 16 is provided at its tip end with a noise microphone 16a and with a noise measuring instrument 16b. A windbreaker screen 16c is provided around the noise microphone 16a. A well-known precision sound level meter unit may be used as the noise measuring unit 16.

The FFT analyzer 18 is an analyzer used to analyze a frequency of a sound pressure signal outputted from the noise measuring unit 16 and to obtain a first resonant frequency f of the face F of the golf club head H, which comprises an input device for acquiring a sound pressure signal of the face F of the golf club head H, the face vibrating due to the impact force imparted thereto, and an analysis unit for obtaining a resonant frequency of the striking face from the sound pressure signal. A well-known frequency analyzer is used as the FFT analyzer 18. The first resonant frequency f obtained by the FFT analyzer 18 is fed to the computer 20.

The computer 20 is used to receive the first resonant frequency f obtained by the FFT analyzer 18, to calculate the coefficient of restitution e on the basis of a lookup table or the formula expressing a relationship between the first resonant frequency f and the coefficient of restitution e which is stored in the computer 20 and to evaluate the restitution characteristics of the golf club head H.

First of all, in such an evaluation system 10, the face F of the golf club head H is vibrated by an impact force of the input force jig 14. At this time, it is preferable that a hosel portion of a golf club 12 is suspended in the air from, for example, a ceiling to form a free end. However, it is possible to lightly fix and support the shaft S of the golf club 12. It is sufficient to adopt such a fixing method that the face F of the golf club head H does not affect the resonant frequencies when the face F is vibrated like a membrane, as will be described later.

On the other hand, the striking sound of the face F upon the vibration (impact vibration) is measured and acquired by the noise microphone 16a of the noise measuring unit 16 arranged in the vicinity of the face F and calibrated by a piston phone or the like in advance and is outputted to the FFT analyzer 18 as the sound pressure signal from the noise measuring instrument 16b.

The frequency analysis is carried out by the FFT analyzer 18 in a narrow bandwidth of, for example, 4,000 to 7,000 Hz.

Figure 2:
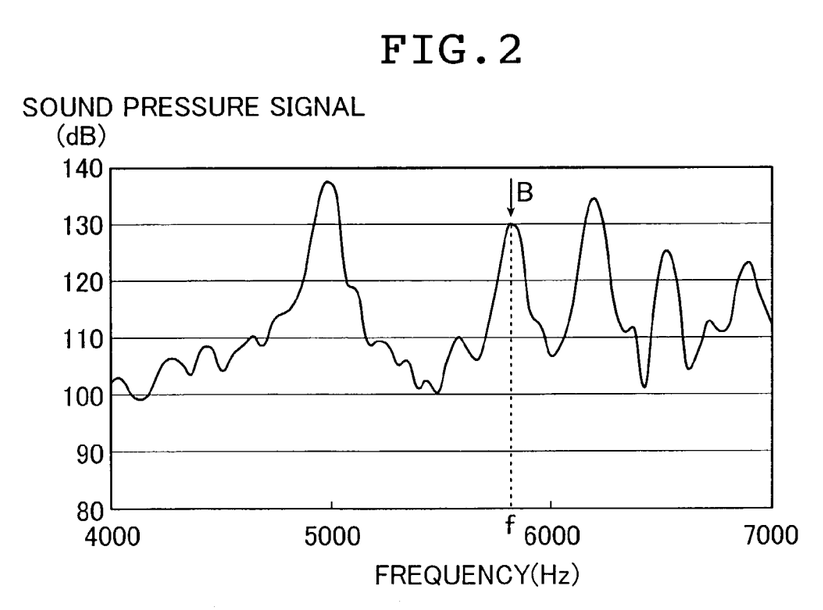
FIG. 2 is a view showing an example of a result of frequency analysis of a sound pressure signal obtained by the evaluation system shown in FIG. 1.

In the frequency analysis, for example, a sound pressure spectrum waveform shown in FIG. 2 is obtained. Five peaks are generated in the bandwidth of 4,000 to 7,000 Hz in the sound pressure waveform. So, the frequency range where the first resonant frequency f is expected to generate may be set in advance to, for example, 5,200 to 6,200 Hz according to a brand of the golf club 12, a commercial model, a type of a golf club or a golf club number a #1 (driver) or a #3 (spoon), and it is possible to identify and obtain the first resonant frequency f from the frequency waveform of the sound pressure signal.

Also, in the case where it is impossible to set such a frequency range in advance and it is impossible to identify and obtain a first resonant peak, the resonant peak can be identified according to the following method.

Since the first resonant frequency f exists in the frequency range of 4,000 to 7,000 Hz, the method utilizes the fact that the information of the first resonant peaks is included not only in the sound pressure signal but also in a vibration of the face F.

Figure 3:
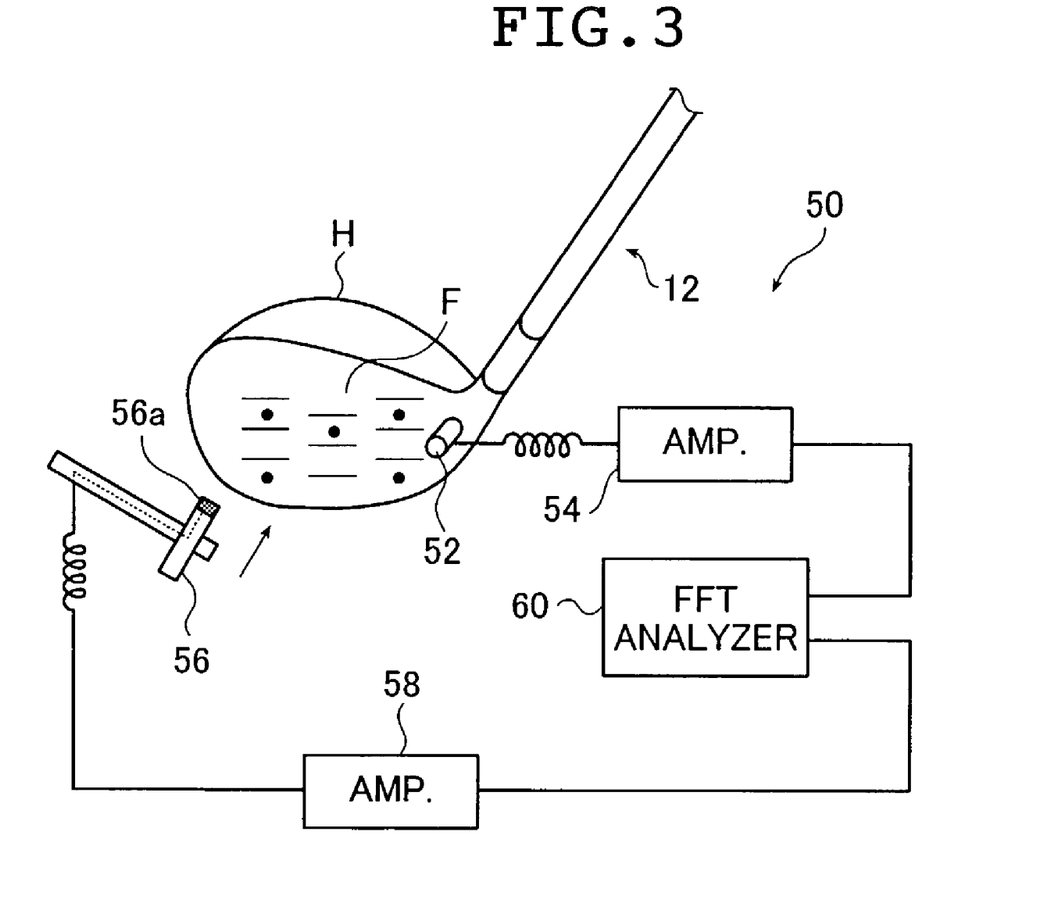
FIG. 3 is a view showing an example of another evaluation system for carrying out a method of evaluating restitution characteristics of the golf club head according to the present invention.

Namely, as shown in FIG. 3, an acceleration pickup 52 is attached to the face F of the golf club head H, and the impact vibration is applied to the face F by using an impact hammer 56. An acceleration signal obtained through an amplifier 54 from the acceleration pickup 52, and the impact signal of the impact force obtained through an amplifier 58 by using a pickup 56a of the impact hammer 56 for measuring the impact force are introduced into an FFT analyzer 60, to thereby obtain a function of the acceleration signal to the impact signal, i.e., a transfer function by the FFT analyzer 60. At this time, impact points by the impact hammer 56 are diffused on the face F of the golf club head H for the impact vibration (at the positions indicated by solid black circles ● on the face F in FIG. 3, for example) to thereby obtain a transfer function according to each of the impact points. In a plurality of transfer functions thus obtained, sharp peaks having the same phase of the vibration caused by a form of a vibration mode of the first resonant frequency of the face F appear at the same frequency irrespective of the impact points. The frequency at the peak position is picked up as the first resonant frequency f.

Figure 4:
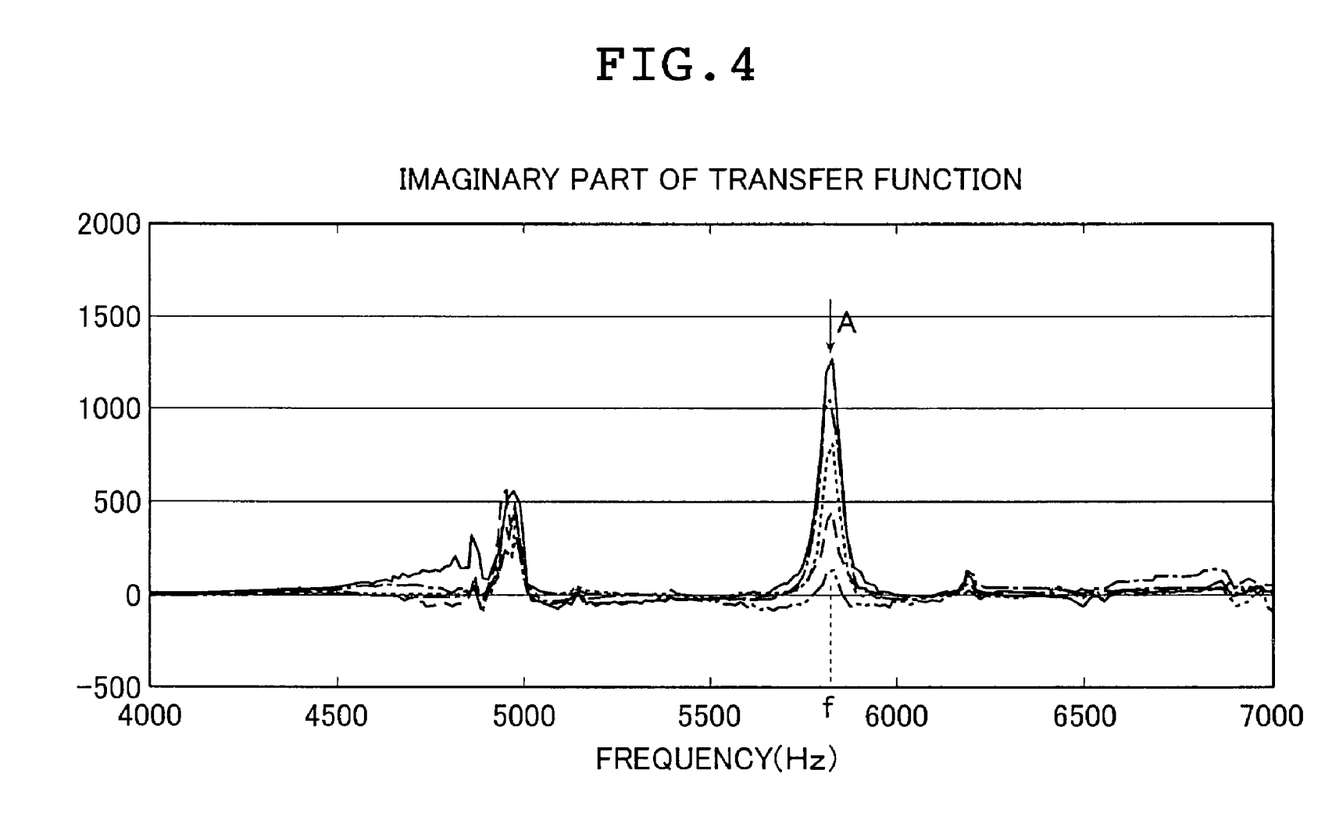
FIG. 4 is a view showing an example of waveform of an imaginary part of a transfer function obtained in accordance with the evaluation system shown in FIG. 3.

For example, FIG. 4 shows waveforms of imaginary parts of the transfer functions when the impact vibrations are performed in five different points on the face F. According to this, it is understood that the imaginary part of the transfer function has sharp maximum peak at a position A to form the resonant peak in each of the five transfer functions. The frequency of this position A is the first resonant frequency f=5,820 Hz.

Also, it is possible to obtain as the first resonant frequency the peak frequency where sharp peaks coincide and have the same phase of the transfer function irrespective of the impact points. The reason why the first resonant frequency may be thus obtained by finding out the sharp peaks having the same phase is that the vibration mode of the first resonant frequency has a deformation in which the face F uniformly moves forward and backward in the perpendicular direction to the face F like a membrane.

Thus, the peak at a position B among the five peaks shown in FIG. 2 becomes the resonant peak by the first resonance of the face F to thereby make it possible to obtain the first resonant frequency f.

Incidentally, the first resonant frequency f found out according to the sound pressure signal may be identified exactly from the transfer function that may be obtained by measuring the acceleration signal. However, the frequency range when the first resonant frequency f is expected to generate is predetermined to, for example, 5,200 to 6,200 Hz according to a brand of the golf club 12, the commercial model, the type of the golf club or the golf club number such as a #1 (driver) or a #3 (spoon), and it is possible to identify and obtain the first resonant frequency f from the frequency waveform of the sound pressure signal.

Incidentally, in the example as shown in FIG. 4, the transfer functions are obtained according to the impact points of the impact vibration to obtain the first resonant frequency f. However, it is possible to take an average of the transfer functions obtained at the impact points to get a single averaged transfer function and to find the first resonant frequency f where the maximum peak of averaged transfer function occurs as the first resonance.

Also, instead of the transfer function, it is possible to identify the first resonant peak from a coherent value of the transfer function to obtain the first resonant frequency f. This is because, since the coherent value of the transfer function shows the characteristic that an amplitude of a response signal is increased near the resonant peak and the coherent value approaches substantially one, it is possible to identify the first resonant peak by utilizing this characteristic.

Figure 5:
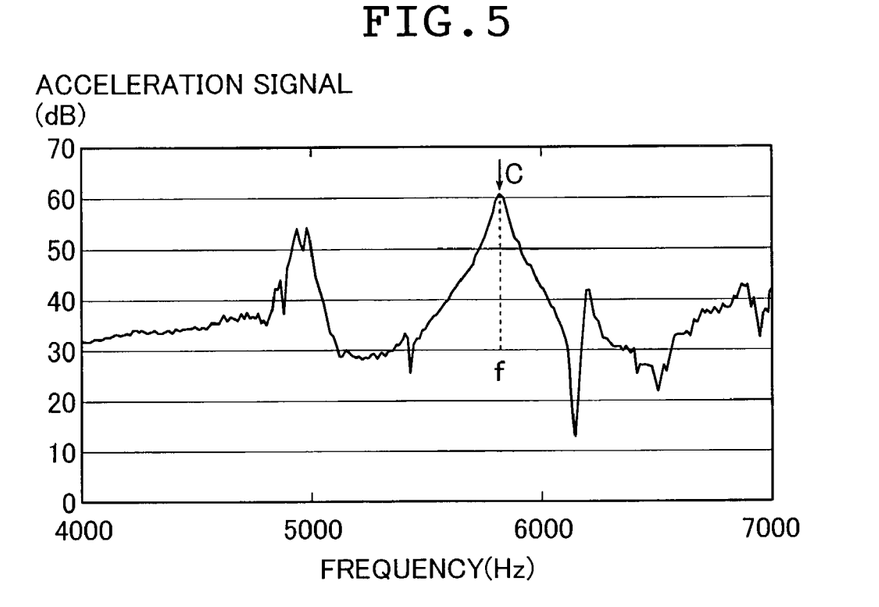
FIG. 5 is a view showing an example of a result of frequency analysis of an acceleration signal obtained in accordance with the evaluation system shown in FIG. 3.

FIG. 5 shows an example of a waveform of the acceleration signal obtained in FIG. 3. The first resonant peak occurs in a position C.

In any of the examples as described above, the first resonant frequency f is identified by the frequency analysis in the frequency range of 4000 to 7000 Hz, although the present invention is not limited to such a frequency range. For example, the frequency range is 3000 to 7000 Hz and frequency analysis may be carried out in this frequency range to obtain the resonant frequency in the range of 3000 to 7000 Hz.

The first resonant frequency f of the face F of the golf club head H thus obtained is fed to the computer 20.

In the computer 20, which is provided with a calculating unit for calculating the coefficient of restitution e from the first resonant frequency f, the restitution being performed when a golf ball is struck by the face F, a squared value of the first resonant frequency f thus fed is obtained. The coefficient of restitution e, which may be obtained according to the method indicated by the USGA shown in FIG. 8, is inferred and calculated on the basis of the reference table or the formula determined in advance within the computer 20 by using the squared value (first resonant frequency f)$^2$.

The reason why the coefficient of restitution e of the golf ball may be inferred and calculated is that the fact the (first resonant frequency f)$^2$ has a very strong correlation with the coefficient of restitution e, which is determined by the method shown in FIG. 8, irrespective of brands or types of the golf club manufacturers is found out by the inventors of the present invention.

Figure 6:
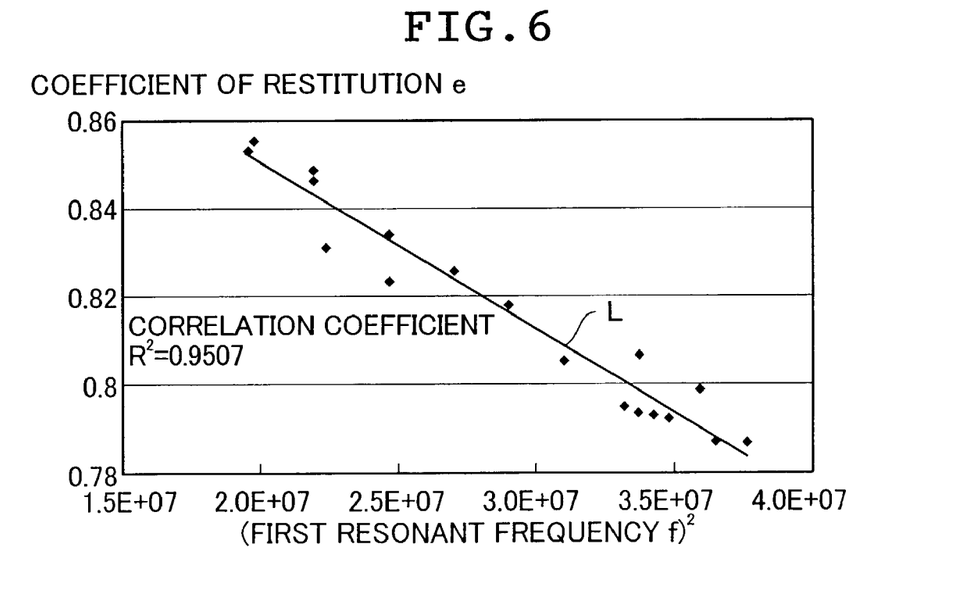
FIG. 6 is a view showing an example of a relationship between a first resonant frequency and a coefficient of restitution obtained in accordance with the evaluation system shown in FIG. 1.

FIG. 6 shows an example of the relationship between the (first resonant frequency f)$^2$ and the coefficient of restitution e of the face F against the golf ball.

The sign ♦ shown in FIG. 6 represents the squared value of the first resonant frequency f of the face F of the golf club head H of various golf clubs different in golf club manufacturers, brands or types and the coefficient of restitution e obtained according to the method shown in FIG. 8.

According to this, in the various golf club heads different in golf club manufacturers, brands or types, the first frequency f is ranged substantially from 4,400 to 6,200 Hz, and the coefficient of restitution e of the face F against the golf ball has the linear correspondence relationship with the squared value of the first resonant frequency f with the correlation coefficient $R^2$ of 0.9507. It is possible to infer the coefficient of restitution e by using such a linear regression formula L and to evaluate whether or not the coefficient of restitution e meets the rule stipulated by the USGA, i.e., the condition that the coefficient of restitution e be equal to or less than 0.830.

Incidentally, in this embodiment, the squared value of the first resonant frequency f is used in inference and evaluation of the coefficient of restitution e. This is because the coefficient of restitution e is considered to change in response to the vibration energy of the face F. The present invention is not limited to the case where the squared value of the first resonant frequency f is used to infer and evaluate the coefficient of restitution e and it is possible to infer and calculate the coefficient of restitution e from, for example, the first resonant frequency f.

Also, the present invention is not always limited to the first resonant frequency but may be a resonant frequency such as a second or a third frequency of the face F. However, it is preferable to use the first resonant frequency that is the primary resonant frequency of the face F in view of the stability or accuracy of the resonant frequency.

In the evaluation systems 10 and 50, the first resonant frequency f is obtained using the FFT analyzer 18 or 60, although the present invention is not limited to such a configuration. A dedicated circuit may be incorporated into the computer 20 that has the function identical to that of an analyzer which is used to analyze the frequency of a sound pressure signal to obtain the first resonant frequency f of the face F of the golf club head H, or alternatively, a program executable in the computer 20 may be stored in the computer 20 and executed so that the function identical to that of the analyzer 18 or 60 as above may be effected with a software.

Figure 7A:
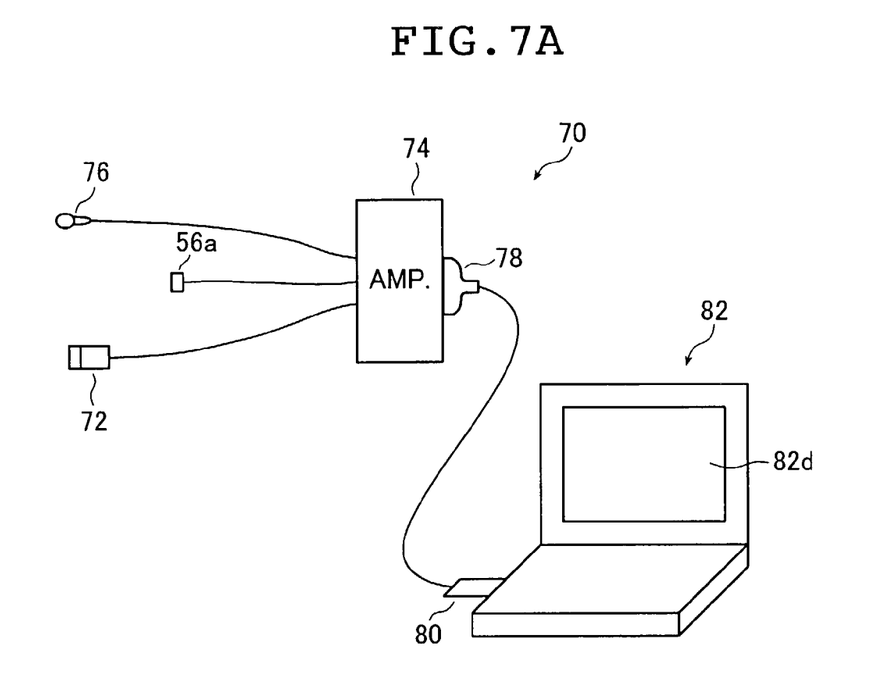
FIGS. 7A and 7B are diagrams showing another example of the system for evaluating restitution characteristics of a golf club head according to the present invention.
Figure 7B:
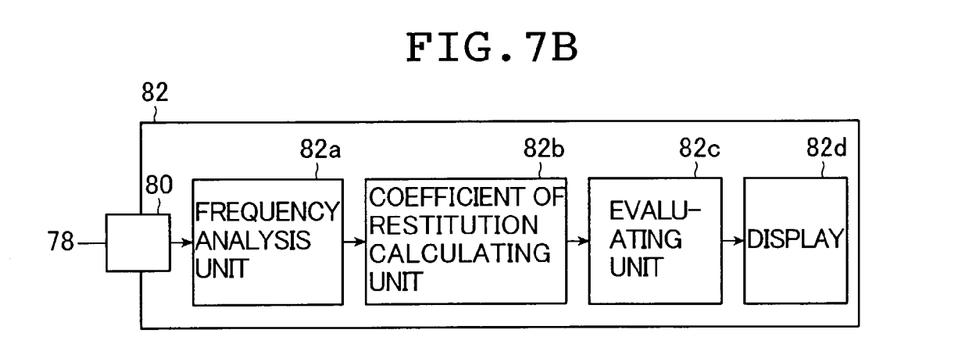

As an example, an evaluation system 70 as shown in FIGS. 7A and 7B may be mentioned.

The evaluation system 70 comprises a small-sized capacitor microphone 72, an amplifier 74, an analog input/output card (input device) 80, a frequency analysis unit 82a, a coefficient of restitution calculating unit 82b, an evaluating unit 82c, and a display 82d.

The amplifier 74 amplifies a sound pressure signal from the capacitor microphone 72 and the analog input/output card (input device) 80 connected with the amplifier 74 through a connecter 78 performs an analog-to-digital conversion of the amplified sound pressure signal, the sound pressure signal thus digitized being fed to the computer 82.

The frequency analysis unit 82a analyzes the frequency of the sound pressure signal fed via the analog input/output card 80 to obtain the first resonant frequency f of the face F of the golf club head H.

The coefficient of restitution calculating unit 82b calculates the coefficient of restitution e from the obtained first resonant frequency f on the basis of the lookup table or the formula expressing the relationship between the first resonant frequency f and the coefficient of restitution e, which is stored in advance.

The evaluating unit 82c evaluates the restitution characteristics of the golf club head H as passing or failing on the basis of the calculated coefficient of restitution e. The calculated coefficient of restitution e and the results of evaluation are displayed on the display 82d.

In this example, the frequency analysis unit 82a, the coefficient of restitution calculating unit 82b, and the evaluating unit 82c are those units which are caused to operate by the execution of a program in a mobile computer 82 and the analog input/output card 80 is being inserted into a predetermined slot of the computer 82. That is to say, the analog input/output card 80, the frequency analysis unit 82a, the coefficient of restitution calculating unit 82b, the evaluating unit 82c, and the display 82d are integrated into the mobile computer 82.

To the amplifier 74 is connected an acceleration pickup 76 and the pickup 56a of the impact hammer 56 as shown in FIG. 3.

It is also possible to use instead of the analog input/output card 80 a circuit board which performs an analog-to-digital conversion of an input signal so as to provide the digitized signal to the frequency analysis unit 82a.

Thus in the evaluation system 70, the first resonant frequency can be obtained by obtaining the sound pressure spectrum waveform from the sound pressure signal acquired using the capacitor microphone 72 or by obtaining the transfer function using the acceleration signal acquired using the acceleration pickup 76, these two methods for obtaining the first resonant frequency being selectively switched from one to the other in the computer 82. Consequently, the coefficient of restitution e can be calculated more efficiently.

Naturally, the evaluation system 70 may have such a configuration that either the capacitor microphone 72 or the acceleration pickup 76 is to be connected.

The capacitor microphone 72 and the amplifier 74 of the evaluation system 70 are discrete components separated from the computer 82. It is, however, also possible in the system 70 to measure the striking sound of the face F of the golf club head H using a built-in microphone of the computer 82, perform processing in the frequency analysis unit 82a, the coefficient of restitution calculating unit 82b and the evaluating unit 82c, and display the results of evaluation on the display 82d.

Thus in the evaluation system 70, processing using a sound pressure signal or an acceleration signal acquired can be carried out with the mobile computer 82. As a result, the method of evaluating restitution characteristics of a golf club head according to the present invention can be easily practiced in a desired place.

Thus, under the condition that the hosel portion of the golf club 12 is suspended in the air or lightly supported, the face F is subjected to the impact force to perform an impact vibration, the sound pressure signal upon this impact vibration is measured and the first resonant frequency of the face F is obtained to thereby make it possible to infer and evaluate the coefficient of restitution e with quite ease and for a short period of time. In addition, it is possible to prevent the removal of the golf club head H away from the shaft S. Accordingly, for a limited period of time before the tournament, it is possible to easily judge whether or not the golf club to be used in a tournament violates the rule of the coefficient of restitution e.

Also, in the case where a large amount of the same golf clubs 12 are to be manufactured in a golf club manufacturer, it is possible to extremely easily examine for a short period of time the coefficient of restitution e of the golf club head H of the golf club 12 that is a complete product in which the shaft S and the golf club head H are integrated. As a result, it is possible to simplify inspection processes for a product performance of the golf club 12 and to reduce the non-uniformity of the product performance of the golf club 12 to be shipped.

In the above-described example, the coefficient of restitution e is inferred and evaluated on the basis of the first resonant frequency of the face F of the golf club head H. Furthermore, the vibration mode upon the first resonance of the face F may be obtained by a well-known modal analysis to obtain a distribution of an amplitude of the vibration by using an amplitude of the transfer function upon the first resonance such as a 70% distribution in which the vibration performs with a 70% of the maximum amplitude of the face F, to thereby make it possible to evaluate the distribution of the restitution characteristics when the golf ball is struck in various positions of the face F. For instance, it is possible to infer and evaluate an effective region of restitution in accordance with the broadness of an occupied area of the 70% distribution.

Thus, it is possible to infer and evaluate the coefficient of restitution e of the golf club 12 with high reliability. It is preferable for the golfer to get satisfied to purchase the golf club 12 whose coefficient of restitution e has been inferred and evaluated by using the above-described first resonant frequency f, on the basis of a brochure for giving information relating to the characteristics of the golf club 12 including the coefficient of restitution e. Also, it is preferable for the golfer to get satisfied to purchase the golf club 12 whose coefficient of restitution e has been inferred and evaluated by using the first resonant frequency f, on the basis of a tag, a sticker, or the like for giving information relating to the characteristics of the golf club 12 including the coefficient of restitution e.

Since the golfer may obtain the information relating to the characteristics from the brochure, the tag or the like and may be informed of the characteristics of the coefficient of restitution e, it is possible for a golfer with a weak power to easily find out the golf club head that is suitable for himself or herself.

The method of evaluating restitution characteristics of the golf club head, the system for evaluating restitution characteristics of the golf club head, and the golf club according to the present invention have been described in detail. However, it is apparent that the present invention is not limited to the above-described embodiment but various improvements and modifications are possible without departing from the scope of the invention. For instance, the coefficient of restitution e of the golf club head H may also be evaluated using a golf club head itself without the shaft S integrated, although in each embodiment as described above is to be evaluated the coefficient of restitution e of the golf club head H of a golf club as a finished product, in which the shaft S and the head H are integral with each other.

As described above in detail, according to the present invention, the striking face of the golf club head is impacted and vibrated and the response signal of the striking face by this impact is acquired to obtain the resonant frequency of the striking face. Accordingly, the coefficient of restitution of the golf club head upon hitting the golf ball can be obtained without removing the golf club head away from the golf club shaft.

In particular, the sound pressure signal is picked up as the response signal, whereby the coefficient of restitution of the golf club head may extremely easily be obtained for a short period of time.

Also, the acceleration of the vibration of the striking face upon the impact vibration is measured and the transfer function is obtained. As a result, it is possible to accurately obtain the first resonant frequency to precisely evaluate the coefficient of restitution.

What is claimed is:

1. A method of evaluating restitution characteristics of a golf club head, comprising:
    preparing a linear regression formula expressing a relationship between resonant frequencies of striking faces of a plurality of samples of golf club heads and coefficients of restitution of the striking faces of the golf club heads of the respective samples;
    imparting an external impact force to a striking face of a golf club head to be evaluated at which a golf ball is hit to cause the striking face to vibrate;
    acquiring a response signal of the striking face which vibrates by the impact force imparted thereto to obtain a resonant frequency of the striking face from the acquired response signal; and
    calculating a coefficient of restitution of the golf club head from the obtained resonant frequency on the basis of the linear regression formula to evaluate a restitution of the golf club head, the restitution occurring when a golf ball is struck by the striking face, wherein the linear regression formula is prepared before the resonant frequency of the striking face of the golf club head to be evaluated is obtained.

2. The method of evaluating restitution characteristics of a golf club head according to claim 1, wherein the resonant frequency is a first resonant frequency of the striking face of the golf club head to be evaluated.

3. The method of evaluating restitution characteristics of a golf club head according to claim 1, wherein the resonant frequency of the golf club head to be evaluated is a frequency of from 3000 Hz to 7000 Hz.

4. The method of evaluating restitution characteristics of a golf club head according to claim 1, wherein the response signal is an acceleration signal of the vibration of the striking face of the golf club head to be evaluated.

5. The method of evaluating restitution characteristics of a golf club head according to claim 4, wherein the impact force is imparted at multiple points on the striking face of the golf club head to be evaluated, a transfer function of the acceleration signal to a signal of the impact force is obtained at each of the points, and a peak frequency at which a peak generates at the same phase in any of the obtained transfer functions at the points is obtained as a first resonant frequency.

6. The method of evaluating restitution characteristics of a golf club head according to claim 4, wherein the impact force is imparted at multiple points on the striking face of the golf club head to be evaluated, and a vibration mode at the resonant frequency is obtained by using an amplitude of a transfer function of the acceleration signal to a signal of the impact force, to evaluate a distribution of the coefficient of restitution of the striking face.

7. The method of evaluating restitution characteristics of a golf club head according to claim 1, wherein the response signal is a sound pressure signal of the striking face of the golf club head to be evaluated.

8. A system for evaluating restitution characteristics of a golf club head, comprising:
    an input device which acquires a response signal of a striking face of a golf club head to be evaluated, the striking face being vibrated by an impact force imparted thereto;
    an analysis unit which obtains a resonant frequency of the striking face from the acquired response signal; and
    a calculating unit which calculates a coefficient of restitution of the golf club head, the restitution occurring when a golf ball is struck by the striking face;
    wherein the calculating unit stores a linear regression formula expressing a relationship between resonant frequencies of striking faces of a plurality of samples of golf club heads and coefficients of restitution of the striking faces of the golf club heads of the respective samples, the linear regression formula being used to calculate the coefficient of restitution from the obtained resonant frequency on the basis of the linear regression formula to evaluate a restitution of the golf club head and the linear regression formula is prepared before the resonant frequency of the striking face of the golf club head to be evaluated is obtained.

9. The system according to claim 8, wherein the response signal is an acceleration signal of the vibration of the striking face of the golf club head to be evaluated.

10. The system according to claim 8, wherein the response signal is a sound pressure signal of the striking face of the golf club head to be evaluated.

11. The system according to claim 8, wherein the input device, the analysis unit and the calculating unit are integrated into a mobile computer.

12. A golf club, in which a restitution characteristic of the golf club head has been evaluated by using a method, comprising:
    preparing a linear regression formula expressing a relationship between resonant frequencies of striking faces of a plurality of samples of golf club heads and coefficients of restitution of the striking faces of the golf club heads of respective samples;
    imparting an external impact force to a striking face of the golf club head at which a golf ball is hit to cause the striking face to vibrate;
    acquiring a response signal of the striking face which vibrates by the impact force imparted thereto to obtain a resonant frequency of the striking face from the acquired response signal; and calculating a coefficient of restitution of the golf club head from the obtained resonant frequency on the basis of the linear regression formula to evaluate a restitution of the golf club head, the restitution occurring when a golf ball is struck by the striking face, wherein the linear regression formula is prepared before the resonant frequency of the striking face of the golf club head is obtained.

13. The method of evaluating restitution characteristics of a golf club head according to claim 1, wherein the resonant frequencies of the striking faces of the plurality of samples are obtained by acquiring response signals of the striking faces as a result of being vibrated by imparting external impact forces to the striking faces respectively.

14. The method of evaluating restitution characteristics of a golf club head according to claim 1, wherein the linear regression formula is a relationship between a resonant frequency and a coefficient of restitution or a relationship between the square of a resonant frequency and a coefficient of restitution.

* * * * *